US008704197B2

(12) United States Patent
Gemmel

(10) Patent No.: US 8,704,197 B2
(45) Date of Patent: Apr. 22, 2014

(54) ACCELERATOR AND METHOD FOR IRRADIATING A TARGET VOLUME

(75) Inventor: Alexander Gemmel, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 348 days.

(21) Appl. No.: 13/171,710

(22) Filed: Jun. 29, 2011

(65) Prior Publication Data

US 2012/0161038 A1 Jun. 28, 2012

(30) Foreign Application Priority Data

Jun. 30, 2010 (DE) .......................... 10 2010 025 660

(51) Int. Cl.
*A61N 5/00* (2006.01)
*G21G 5/00* (2006.01)

(52) U.S. Cl.
USPC ................. 250/492.3; 250/492.1; 250/493.1; 250/505.1; 250/396 R; 250/398

(58) Field of Classification Search
USPC ......... 250/492.1, 492.3, 493.1, 505.1, 396 R, 250/398
See application file for complete search history.

(56) References Cited

U.S. PATENT DOCUMENTS

2010/0001212 A1    1/2010 Nishiuchi et al.

FOREIGN PATENT DOCUMENTS

DE    10 2007 045 879 A1    4/2009
EP     0 779 081 A2          6/1997

OTHER PUBLICATIONS

Furukawa, T., Inaniwa,T., Sato,S., Tomitani,T., Minohara,S., Noda, K., and Kanai,T. "Design study of a raster scanning system for moving target irraditation in heavy-ion radiatherapy", Medical Physics, vol. 34, No. 3, Mar. 2007, pp. 1085-1097.*
German Office Action dated Mar. 15, 2011 for corresponding German Patent Application No. DE 10 2010 025 660.9-54 with English translation.
Yoshikazu Tsunashima et al., "Efficiency of respiratory-gated delivery of synchrotron-based pulsed proton irradiation," Physics in Medicine and Biology 53, pp. 1947-1959, 2008.

* cited by examiner

*Primary Examiner* — Jack Berman
*Assistant Examiner* — Meenakshi Sahu
(74) *Attorney, Agent, or Firm* — Lempia Summerfield Katz LLC

(57) ABSTRACT

A device operable to accelerate a particle beam to an energy for irradiating a target volume. The device includes a particle accelerator operable in a first working phase in which particles of the particle beam are accelerated to the energy and a second working phase in which the particles of the particle beam are provided and extracted for irradiating the target volume. The device further includes a control device operable to interrupt an irradiation of the target volume if the target volume assumes a predetermined state. The control device is also operable to control the particle accelerator as a function of a comparison between a residual particle number stored in the accelerator and a reference value.

20 Claims, 3 Drawing Sheets

ACCELERATOR AND METHOD FOR IRRADIATING A TARGET VOLUME

This application claims the benefit of DE 10 2010 025 660.9, filed Jun. 30, 2010.

BACKGROUND

The present embodiments relate to a device and method for irradiating a target volume with a particle beam.

Particle therapy is an established way to treat tissue (e.g., malignant tumors). Irradiation methods are used in particle therapy, but may also be employed in non-therapeutic fields such as in research activities (e.g., for product development), or on non-living phantoms, bodies or materials.

Irradiation methods may utilize charged particles such as, for example, protons, carbon ions, or other ions. The charged particles are accelerated to high energies, formed into a particle beam, and directed to one or more irradiation rooms by way of a high-energy beam transport system. The particle beam irradiates the object having a target volume in one of the irradiation rooms.

In some cases, however, the target volume that is to be irradiated moves. During the irradiation of a patient, respiratory movement may, for example, cause the tumor to move. For research purposes, this type of movement may be simulated using model objects (e.g., phantoms).

A "gating" irradiation method is a known way to deal with the possibility that the target volume may move. Such a method monitors the motion of the target volume. The particle beam, with which the target volume is irradiated, operates as a function of the monitoring and is thus dependent on the status of the target volume. When the target volume is located within a suitable or desired region, the particle beam is turned on and may be used to irradiate the target volume. When the target volume is located outside of the suitable or desired region, the particle beam is turned off and may not be used for irradiation purposes. In this way, the particle beam is activated, for irradiation purposes, only when the target volume is located in a suitable region.

"Gating" irradiation methods of this type are known, for example, from Tsunashima Y. et al., titled "Efficiency of respiratory-gated delivery of synchrotron-based pulsed proton irradiation", 2008 Phys. Med. Biol. 53 1947.

SUMMARY AND DESCRIPTION

The present embodiments may obviate one or more of the drawbacks or limitations in the related art. For example, an accelerator that provides a particle beam capable of quickly and efficiently irradiating a moving target volume may be provided. An irradiation method that enables fast and efficient irradiation of a target volume may also be provided.

One embodiment of an accelerator that accelerates a particle beam to an energy for irradiating a target volume is a particle accelerator that operates in phases. The working phases of the accelerator may alternate. During operation, the particles are accelerated by the accelerator in a first working phase. The accelerator may be filled with particles, and the accelerator may accelerate the particles to an irradiation energy provided for the irradiation. When the accelerator is in a second working phase following the first working phase, the accelerated particles are stored or circulated in the accelerator and may be provided and extracted for irradiation purposes.

In one embodiment, the accelerator has a control device for controlling the accelerator during the irradiation of the target volume. The control device may operate to interrupt an irradiation of the target volume if the target volume assumes a predetermined state. Following interruption of the irradiation, a residual particle number stored in the accelerator may be compared with a reference value. Operation of the accelerator may be controlled as a function of the result of this comparison.

The accelerator may irradiate the target volume using a gating method, in which the irradiation is interrupted when the target volume assumes a predefined state. For example, the irradiation may be interrupted if it is determined that the position of the target volume has changed to such a degree that an irradiation would cause an incorrect dosage.

Several gating methods are known. For example, an external surrogate motion signal that provides information about the motion status of the target volume may be recorded. By measuring movement of the abdominal wall, the position of the internally located target volume may be inferred. In other examples, actual movement of the target volume may be monitored directly by using, for example, X-ray photographs, fluoroscopic projections, ultrasound imaging or active, implanted transponders.

When the target volume is located outside of a defined spatial region and/or when, in the case of quasi-periodic motion of the target volume, the target volume is situated in a specific phase of the motion cycle, the irradiation process is interrupted. A repeat irradiation of the target volume in a gating method is permitted when the target volume is once again in a further predefined state. This may occur when the target volume reaches a specific location or a specific phase of the motion cycle. Known gating irradiation methods thus apply the particle beam when a so-called gate-on phase is present.

Accelerators that are deployed in a particle therapy context may have different, alternating working phases. In the accelerators, the particle beam is applied if the accelerator is in a phase in which particles have already been accelerated to the irradiation energy. The irradiation methods thus apply the particle beam when the accelerator is in the second working phase as explained above. The target volume is irradiated when the second working phase and the gate-on phase are simultaneously present. This poses a problem when all of the particles having the requisite irradiation energy have been consumed and the particle accelerator switches from the second working phase to the first working phase. In such a case, the irradiation is interrupted until both the gate-on phase and second working phase of the accelerator are simultaneously present again. The remaining time of the gate-on phase, in which an irradiation would otherwise be possible, is lost. Time that is lost due to this unfavorable coordination may lengthen an otherwise typical irradiation time in the case of typical movements of a target volume such as a lung by, for example, 5% to 10% of the total irradiation time.

In the present embodiments, following an interruption of the irradiation of the target volume that occurs when the target volume assumes a predefined state, the residual particle number remaining in the accelerator may be compared with a reference value. In some embodiments, the comparison may occur immediately following an interruption of the irradiation method. The accelerator may be controlled differently depending on the result of the comparison.

A gate-off phase is measured by the time interval between the time instant at which the beam is interrupted (e.g., caused as a result of the target volume having assumed a predefined state) and the following time instant at which the target volume has assumed a second predefined state, in which irradiation is again appropriate, characterizes the gate-off phase. During the gate-off phase, irradiation is not possible. The length of the gate-off phase is dependent on the amount the target volume actually moves. Advantageously, the accelerator control in the present embodiments may, during the gate-off phase following a gate-on phase, prepare the accelerator for one of the following gate-on phases. The comparison of the residual particle number with the reference value may take place at the beginning (e.g., during the first half) of a gate-off phase. If the residual particle number is less than the reference value, the accelerator may be controlled such that the particle accelerator may be switched from the second working phase to the first working phase. Because the accelerator is once more in the first working phase, particles may again be introduced into and accelerated to the requisite irradiation energy within the accelerator. A sufficiently large number of particles for an irradiation may thus be available once again for irradiation purposes when the accelerator returns to the second working phase of the accelerator. Using the method according to the present embodiments, this advantageously takes place at least partially during a gate-off phase. In one embodiment, the residual particle number stored in the accelerator may be discarded if the residual particle number is less than the reference value. In one embodiment, the reference value used for the comparison may be determined from, for example, a required residual particle number for irradiating a sub-region of the target volume. Accordingly, during one of the following gate-on phases, a sufficiently large number of particles will be present in the accelerator to permit irradiation of the sub-region of the target volume in full. The sub-region of the target volume may be an area that is provided for an irradiation with the same particle energy, such as, for example, an iso-energy layer. The particles stored in the accelerator may be extracted for the purpose of irradiating the sub-region.

A method for accelerating a particle beam to an irradiation energy and irradiating a target volume using an accelerator may be performed as follows: (1) the irradiation of the target volume is interrupted if the target volume assumes a predetermined state; (2) following interruption of the irradiation, a remaining or residual particle number stored in the accelerator is compared with a reference value; and (3) the accelerator is controlled as a function of the result of the comparison. The accelerator may be a particle accelerator that operates in a first working phase and a second working phase. In the first working phase, the accelerator accelerates particles to the requisite energy. In the second working phase, the accelerator stores the accelerated particles for irradiation purposes and provides the stored accelerated particles for extraction. The accelerator may be controlled such that the accelerator is switched from the second working phase to the first working phase if the residual particle number is less than the reference value. Depending on the result of the comparison, the residual particle number stored in the accelerator may be discarded. The reference value used for the comparison may be determined from a residual particle number for irradiating a sub-region of the target volume. The sub-region of the target volume may be an area that is provided for irradiation with the same particle energy.

The preceding and following description of the individual features, advantages of the features, and effects of the features relate both to the device category and to the method category, without this explicitly being mentioned in each case. The individual features disclosed in the process may also be used in combinations other than those shown.

DETAILED DESCRIPTION OF THE DRAWINGS

Figure 1:
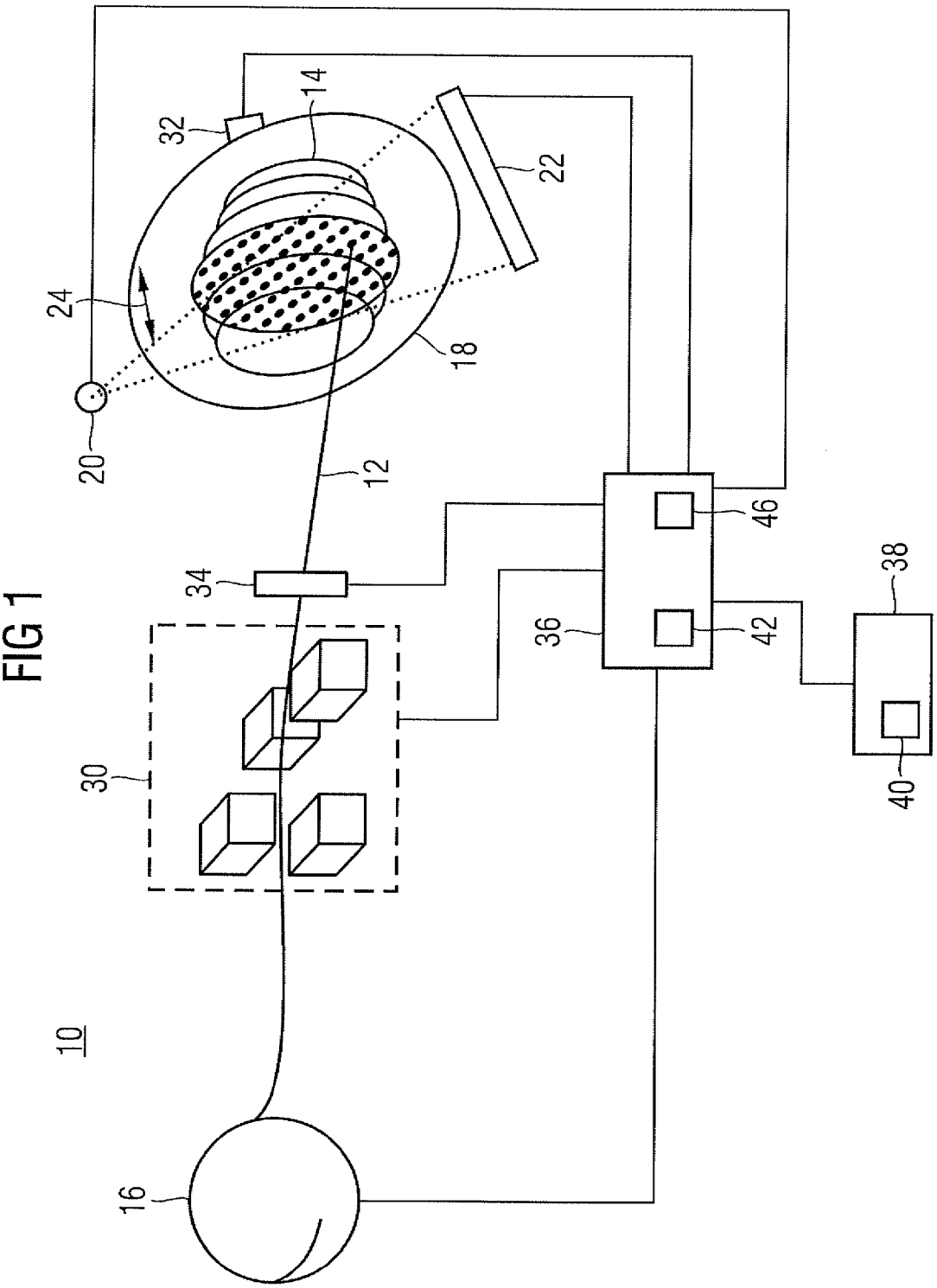
FIG. 1 shows a schematic representation of one embodiment of a particle therapy system for monitoring the motion of a target volume that is to be irradiated.

FIG. 1 shows a particle therapy system 10. The particle therapy system 10 is used for irradiating a body arranged on a positioning device with a particle beam 12. The particle beam 12 may consist of charged particles such as, for example, protons, pions, helium ions, carbon ions, or ions of other elements. Tumor-diseased tissue of a patient, for example, may be irradiated as a target volume 14 with the particle beam 12. The particle beam system 10 may also be used, for example, to irradiate a non-living body such as, for example, a water phantom or other type of phantom, or cell cultures for research or maintenance purposes. The objects that form the target volume 14 may be moving bodies. The target volume 14 may be non-visibly located inside a target object 18 and may move quasi-cyclically within the target object 18.

The particle therapy system 10 may include an accelerator unit 16 (e.g., a synchrotron) that provides a particle beam 12 with energy for the irradiation. Iso-energy layers and target points that are scanned using a raster scanning method during the irradiation may be, as shown in FIG. 1, located in the target volume 14 that is to be irradiated. A raster scanning method, in which the particle beam 12 is guided from target point to target point without being turned off when a transition is made from one target point to the next, may be used as the scanning method. In other embodiments, other scanning methods may be used. The particle beam 12 in the embodiment shown in FIG. 1 is influenced in a lateral deflection with the aid of scanning magnets 30. The particle beam 12 may, for example, be deflected in a direction that is perpendicular to the beam trajectory direction, such as the x- and y-direction. In other embodiments, other irradiation methods may be used. An alternative irradiation method may, for example, utilize passive beam application.

The irradiation system 10 may also include a control device 36 and detectors 34 for monitoring the beam parameters. The control device 36 (e.g., the control system of the irradiation system) controls the individual components of the irradiation system (e.g., the accelerator 16 and the scanning magnets 30). The control device 36 may also be used to turn the particle beam 12 on and off, as desired. The control device 36 collects measurement data such as the data for the detectors 34 for monitoring the beam parameters. The control device may be effected using an irradiation plan 40 that is determined and provided with the aid of an irradiation planning device 38.

In order to detect the motion of the target volume 14, a detection device 32 may be provided to record an external surrogate motion signal. The detection device 32 may be, for example, an abdominal belt. A signal waveform may be recorded based on the distension of the detection device. Using the recorded waveform, the characteristic curve of the respiratory cycle of a patient and the position of a tumor moving with the respiration, may be determined. In addition, an analyzer device 46 may be integrated in the control device 36 and may evaluate the surrogate motion signal recorded by the detection device 32. The analyzer device 46 may, for example, determine a gating window with the aid of the surrogate motion signal.

In order to detect the motion 24 of the target volume 14, a fluoroscopy device may also be provided. The fluoroscopy device may include a radiation source 20 and a radiation detector 22. The radiation detector 22 may produce continuous or individual X-ray photographs of the target volume 14. In one embodiment, an image evaluation device 42 may be integrated into the control device 36, thus enabling the image data of the fluoroscopy device to be analyzed and compared with other image data.

Figure 2:
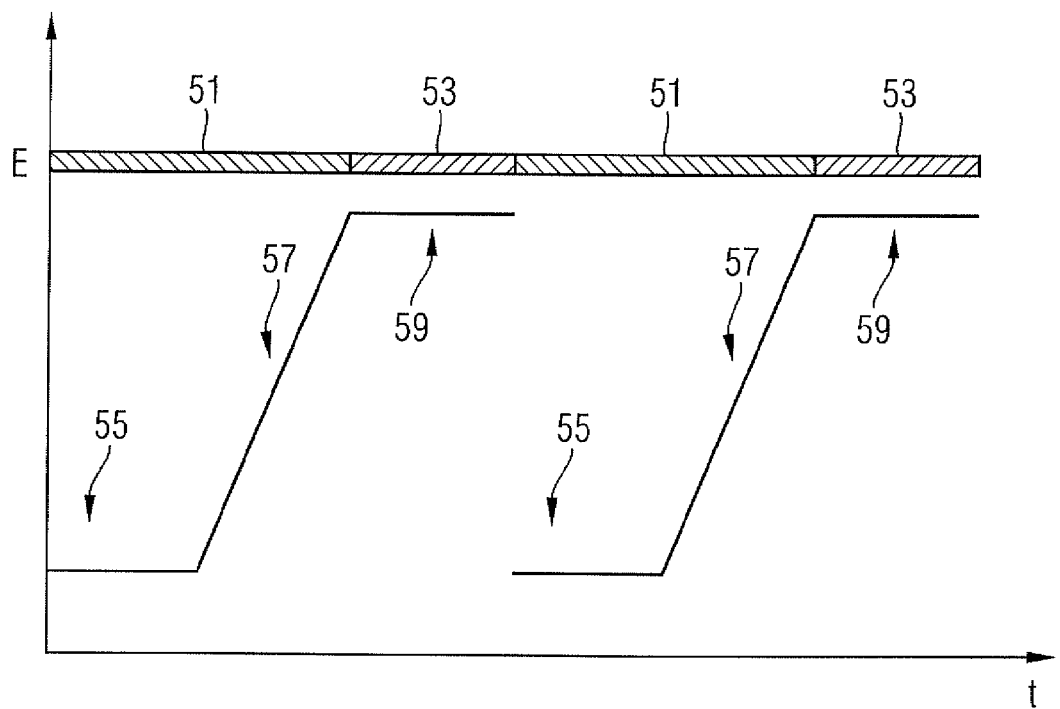
FIG. 2 shows a schematic representation of a time sequence of different working phases of one embodiment of a synchrotron accelerator.

FIG. 2 depicts different working phases of a synchrotron. FIG. 2 shows the particle energy E of the particles in the synchrotron as a function of the time t. A synchrotron is an accelerator that has two different working phases. In a first working phase (bar 51), particles are guided into the synchrotron (act 55) until the synchrotron is filled. In act 57 of the first working phase, the particles guided into the synchrotron are accelerated to a particle energy sufficient for irradiation purposes. In the first working phase, the particles may not be extracted.

After the synchrotron is filled with accelerated particles, the particle accelerator may transition to a second working phase (bar 53). In the second working phase, the target volume may be irradiated. The particles circulate or are "stored" in the synchrotron at the energy to which the particles have been accelerated (act 59). The particles may be extracted from the accelerator and directed to irradiate the target volume. As soon as the particles are consumed or a new energy is to be set, the particle accelerator may transition back to the first working phase.

Figure 3:
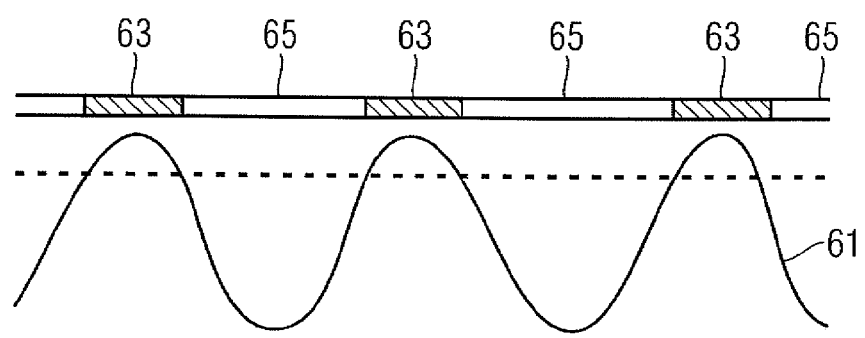
FIG. 3 shows a schematic representation of an example quasi-periodic motion of a target volume with gate-on phases and gate-off phases.

FIG. 3 shows the periodic or quasi-periodic motion 61 of a moving target volume. The motion of the target volume may, for example, be caused by a respiratory cycle that raises and lowers the target volume. The motion of the target volume may be subdivided into gate-on phases 63 and gate-off phases 65. During the gate-on phase 63, the position or orientation of the target volume is such that an irradiation may be performed without an appreciably incorrect irradiation of the target volume taking place. During the gate-off phase 65, the irradiation of the target volume should be interrupted, as an irradiation during this phase would lead to a mis-delivery of the dose. The beginning of the gate-on phase 63 or the gate-off phase 65 may be determined using known devices. For example, the detection device 32 or the above-described fluoroscopy device may be used.

When the accelerator is in the appropriate working phase (e.g., the second working phase), and the target volume is simultaneously in the gate-on phase, the target volume may be irradiated. The presence of the gate-on phase may be independent of the phase of the accelerator cycle.

When the target volume is in the gate-on phase, but the synchrotron is not full of particles, the irradiation is interrupted. Accordingly, no further extraction may take place, and the synchrotron transitions from the second working phase to the first working phase. This transition occurs even though the gate-on phase is still present, because the synchrotron is totally discharged and all the particles are "consumed." In this situation, the gate-on phase is not effectively utilized, and the remaining time of the gate-on phase is not used.

Figure 4:
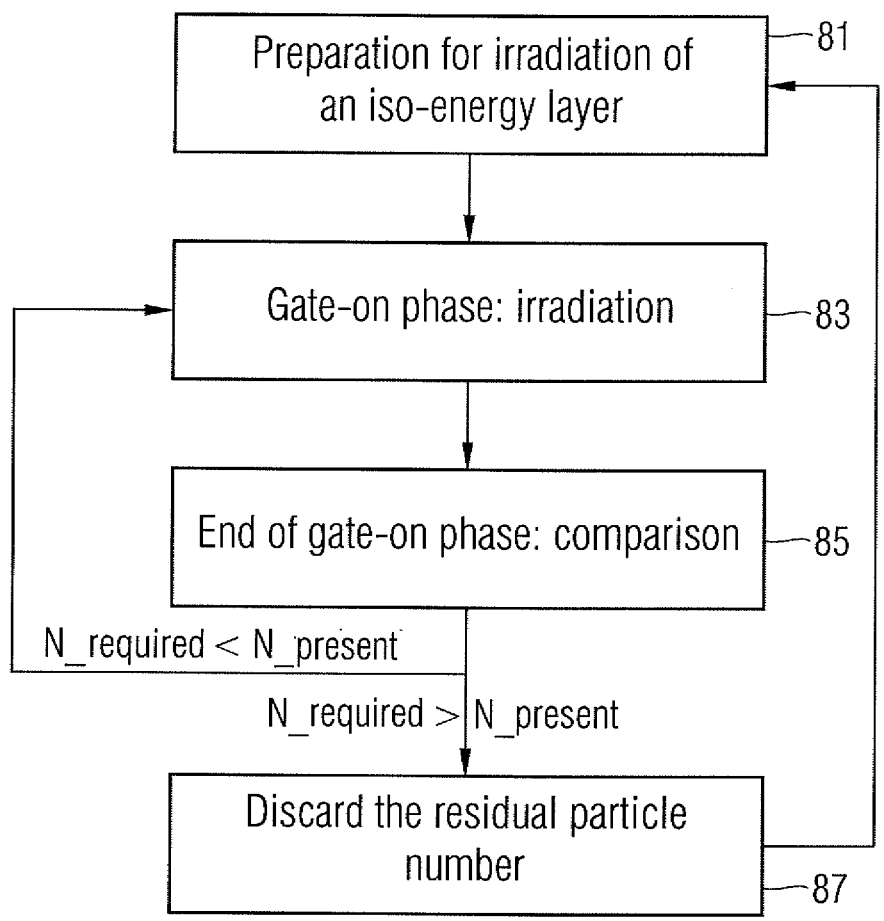
FIG. 4 shows a flowchart of one embodiment of an irradiation method.

To prevent interruption of the irradiation method, the method shown in FIG. 4 is performed. In this embodiment, an iso-energy layer of the target volume may be irradiated with a predefined dose using the scanning method.

The accelerator may be filled completely with particles, and the particles may be accelerated to a predefined energy for the irradiation of the iso-energy layer (act 81). The iso-energy layer may be irradiated during the gate-on phase (act 83). Following termination of the gate-on phase (act 85), a comparison may be performed, in which the residual particle number (N_present) contained or stored in the synchrotron may be compared with the particle number to irradiate the remainder of the iso-energy layer (N_required).

If the comparison establishes that the residual particle number is sufficient for irradiating the remaining iso-energy layer (N_required<N_present), the irradiation may continue as soon as the next gate-on phase begins (return to act 83). If the comparison reveals that the residual particle number present in the synchrotron is not sufficient for irradiating the remaining iso-energy layer (N_present<N_required), the residual particle number still present in the synchrotron may be discarded (act 87).

The synchrotron may be refilled with particles that are thereupon accelerated to the irradiation energy (return to act 81). The irradiation may continue once the synchrotron returns to the second working phase, and the gate-on phase is simultaneously present (act 83). These acts may be repeated until the iso-energy layer has been irradiated in full. Following these acts, an additional iso-energy layer may then be irradiated.

The above-described unfavorable scenario for the irradiation may, therefore, be avoided, or at least minimized, if the information concerning the charge state and/or the fill level of the synchrotron is taken into account in the course of controlling the accelerator (e.g., following termination of each extraction for the accelerator).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for accelerating a particle beam to an energy for irradiating a target volume, the device comprising:
   a particle accelerator operable in a first working phase and a second working phase, particles of the particle beam being accelerated to the energy in the first working phase and the particles of the particle beam being provided and extracted for irradiating the target volume in the second working phase; and
   a control device configured to:
      monitor a motion of the target volume;
      interrupt an irradiation of the target volume when the target volume assumes a predetermined position or orientation that is determinable based on the monitored motion; and
      control the particle accelerator as a function of a comparison between a residual particle number stored in the particle accelerator and a reference value.

2. The device as claimed in claim 1, wherein the control device is operable to switch the particle accelerator from the second working phase to the first working phase if the residual particle number is less than the reference value.

3. The device as claimed in claim 2, wherein the reference value used for the comparison is determined from a residual particle number that is required for irradiating a sub-region of the target volume.

4. The device as claimed in claim 1, wherein the control device is operable to discard the residual particle number stored in the particle accelerator if the residual particle number is less than the reference value.

5. The device as claimed in claim 2, wherein the control device is operable to discard the residual particle number stored in the particle accelerator if the residual particle number is less than the reference value.

6. The device as claimed in claim 4, wherein the reference value used for the comparison is determined from a residual particle number that is required for irradiating a sub-region of the target volume.

7. The device as claimed in claim 6, wherein the sub-region of the target volume is an area which is to be irradiated with the same particle energy.

8. The device as claimed in claim 1, wherein the reference value used for the comparison is determined from a residual particle number that is required for irradiating a sub-region of the target volume.

9. The device as claimed in claim 8, wherein the sub-region of the target volume is an area which is to be irradiated with the same particle energy.

10. A method for irradiating a target volume, the method comprising:
    accelerating particles of a particle beam to an irradiation energy provided for the irradiation of a target volume in a first working phase of a particle accelerator;
    irradiating the target volume using the accelerated particles in a second working phase of the particle accelerator;
    monitoring a motion of the target volume;
    interrupting the second working phase of the particle accelerator when the target volume assumes a predetermined position or orientation that is determinable based on the monitored motion;
    comparing, following the interrupting, a remaining residual particle number stored in the accelerator with a reference value; and
    controlling the particle accelerator as a function of a result of comparing the remaining residual particle number with the reference value.

11. The method as claimed in claim 10, wherein controlling comprises switching the particle accelerator from the second working phase to the first working phase if the residual particle number is less than the reference value.

12. The method as claimed in claim 11, wherein controlling comprises discarding the residual particle number stored in the particle accelerator if the residual particle number is less than the reference value.

13. The method as claimed in claim 10, wherein controlling comprises discarding the residual particle number stored in the particle accelerator if the residual particle number is less than the reference value.

14. The method as claimed in claim 10, wherein comparing comprises determining the reference value based on a residual particle number that is required for irradiating a sub-region of the target volume.

15. The method as claimed in claim 14, wherein the sub-region of the target volume is an area which is provided for irradiation with the same particle irradiation energy.

16. The method as claimed in claim 11, wherein comparing comprises determining the reference value based on a residual particle number that is required for irradiating a sub-region of the target volume.

17. The method as claimed in claim 16, wherein the sub-region of the target volume is an area which is provided for irradiation with the same particle irradiation energy.

18. The method as claimed in claim 13, wherein comparing comprises determining the reference value based on a residual particle number that is required for irradiating a sub-region of the target volume.

19. The method as claimed in claim 18, wherein the sub-region of the target volume is an area which is provided for irradiation with the same particle irradiation energy.

20. The device as claimed in claim 1, wherein the control device is configured to control the particle accelerator as a function of the comparison following interruption of the irradiation.

* * * * *